United States Patent [19]
Hollinger

[11] Patent Number: 5,437,200
[45] Date of Patent: Aug. 1, 1995

[54] LIQUID METERING AND TRANSFER VALVE ASSEMBLY PARTICULARLY FOR FLOW CYTOMETER

[75] Inventor: John D. Hollinger, Miami, Fla.

[73] Assignee: Coulter Corporation, Miami, Fla.

[21] Appl. No.: 4,812

[22] Filed: Jan. 15, 1993

[51] Int. Cl.[6] ............................................. G01N 1/30
[52] U.S. Cl. ................................................ 73/863.73
[58] Field of Search ............ 73/865.5, 863.73, 864.83, 73/864.84; 422/103; 324/71.4; 356/441, 442; 377/10

[56] References Cited

U.S. PATENT DOCUMENTS

| | | |
|---|---|---|
| 3,380,584 | 4/1968 | Fulwyler . |
| 3,567,389 | 3/1971 | Coulter et al. . |
| 3,567,390 | 3/1971 | Rothermel . |
| 3,963,606 | 6/1976 | Hogg . |
| 3,989,381 | 11/1976 | Fulwyler . |
| 4,038,556 | 7/1977 | Auer et al. . |
| 4,041,385 | 8/1977 | Gulliford et al. ............... 324/71.4 |
| 4,230,031 | 10/1980 | Pedroso et al. . |
| 4,230,558 | 10/1980 | Fulwyler . |
| 4,395,676 | 7/1983 | Hollinger et al. . |
| 4,445,391 | 5/1984 | Cabrera . |
| 4,577,515 | 3/1986 | Someya et al. . |
| 4,730,155 | 3/1988 | Hoggs ............................. 324/71.4 |
| 4,957,008 | 9/1990 | Proni et al. . |
| 4,981,580 | 1/1991 | Auer . |
| 5,270,212 | 12/1993 | Horiuchi et al. ................ 73/863.73 |

Primary Examiner—Robert Raevis
Attorney, Agent, or Firm—Sidney N. Fox; John T. Winburn; Mitchell E. Alter

[57] ABSTRACT

A metering and transfer valve assembly particularly for use in particle analyzing apparatus for the study of particles in liquid suspension, the valve assembly having at least pair of inner and outer valve elements coaxially arranged in face to face frictional sealing engagement with a center valve element, each of the valve elements being independently rotatable, first passages defining a first flow path through the assembly, second passages defining a second flow path through the assembly, the first passages including a metering chamber for measuring and transferring a precise sample aliquot of sample flowing in the first flow path into the second flow path, the first flow path leading to a first exterior location and the second flow path leading to a second exterior location, and a drive fluid being introduced to the second flow path subsequent to transfer of said aliquot thereto for propelling said aliquot along the second flow path to the second esterior destination, the second destination being a flow scanning cell whereby an absolute count of the full content of said aliquot can be established. The first destination can be a flow scanning cell and the first flow path can lead liquid sample to said flow scanning cell before the aliquot is transferred to said path. A method of cytometric analysis is described as well as apparatus utilizing said valve assembly.

5 Claims, 12 Drawing Sheets

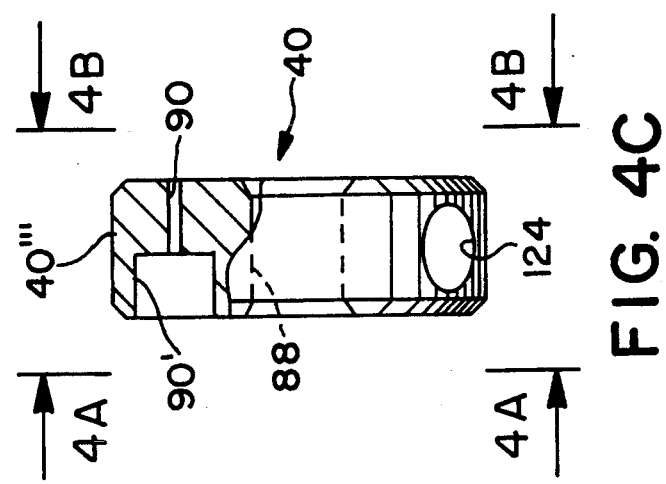
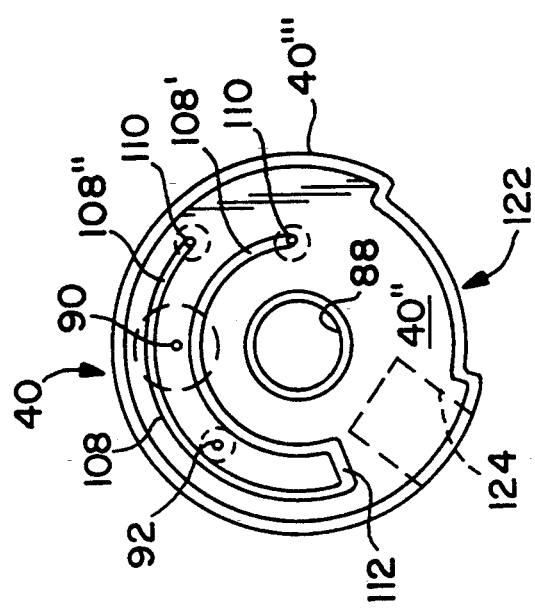
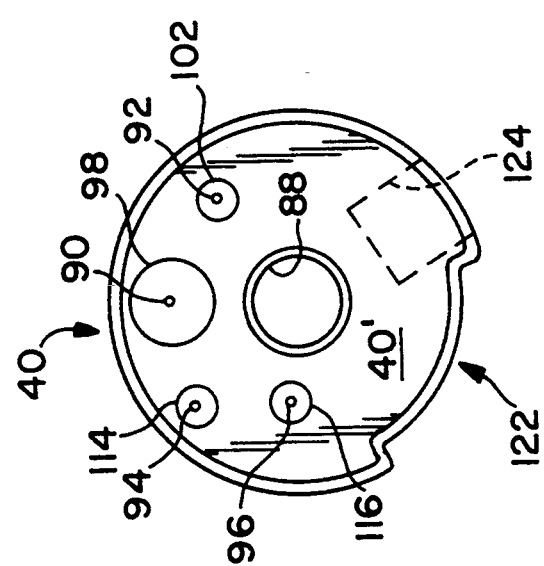

LIQUID METERING AND TRANSFER VALVE ASSEMBLY PARTICULARLY FOR FLOW CYTOMETER

FIELD OF THE INVENTION

This invention relates generally to flow cytometry and more particularly provides a sample metering and transfer valve assembly for transferring a liquid sample directly to the flow cell of a focussed flow cytometer and subsequently metering and transferring a precise aliquot portion of the same liquid sample to the same flow cell enabling the provision of the normal particle scans and the obtaining of a total count of selected particles within the said aliquot per volume of said aliquot, to provide thereby an Absolute Count, data highly important as a factor in predicting and monitoring clinical disease progression and treatment.

The development of flow cytometers has been significant for providing information relating to the identification and obtaining the differential relationships between biological particles, such as blood cell types including lymphocytes, monocytes and granulocytes, as well as subsets thereof.

Recently, there has been extensive reliance upon flow cytometry for providing precise identification of such biological particles, such as these cell types and populations and sub-populations which have been linked to specific immune functions. The clinical relevance of lymphocyte population measurements, such as lymphocytes, for example, known as immunophenotyping, has been established for a number of different disorders and diseases. Alterations in numbers of cells of a specific lineage, such as CD4+ lymphocyte cells, may suggest a diagnosis of leukemia, lymphoma or immunodeficiency. Small numbers of unusual cells can be identified as having aberrant or disease-specific phenotypes. While such information cannot be the basis of a clinical diagnosis, results of this type of cell analysis provide entry into the body of information used to make a diagnosis.

Such information is believed highly useful in monitoring, evaluating and/or predicting clinical responses in patients receiving experimental therapies against many infectious diseases, cancers, immunodeficiencies, etc. Meaningful data can be obtained from such information which relate to stages reached in a disease and to determine when changes occur in a particular stage development of a disease, providing critical factors in monitoring the treatment of such disease. The relative proportion of lymphocyte subsets, such as depletion of SD4+ subset of T-lymphocytes during the course of HIV infection can be altered during the course of such infection and is frequently used to assess the immunological status of individuals so infected. It is important that the many individual laboratories measure such phenotypic data with great precision and accuracy possible. There is considerable differences between instruments and reagents employed in the many laboratories performing such measurements. Improvements in agreement between these many laboratories have been made but the precision obtained is not as fine as required reliably to detect small but clinically significant changes in these key parameters. Many factors contribute to these problems but a major contributing factor is that the values required to make the necessary computations cannot be obtained from a single type instrument. Performance, say of white blood cell counts and differential counts are routinely performed in different laboratories, on separate blood samples, using instruments built around different technologies.

Additionally, obtaining repeated identification data over elapse of time, for following select different cell/volume ratios also is significant in monitoring both progressive diseases and the therapeutic treatment thereof. A key factor in providing such markers for accurately predicting such clinical responses, say for persons receiving experimental therapies, monitoring the effect of such therapies and the state of the diseases, for example, may be the provision of absolute counts of such cell numbers, for example, on immunophenotyping specimens. Performing absolute counts on any sample requires that all the particles/cells in a precisely measured volume, are counted. Knowing such count and knowing the volume containing the particles and the dilution ratio allows the calculation of the count of all the particles/cells in the original medium.

Traditional methods of counting, such as for example, use of the Coulter Counter, measure the precise volume containing the particles of interest by precisely timing or measuring the flow of a suspension of the particles through an aperture. All the particles in such suspension drawn through the aperture are counted. This method typically employs either maintaining precise pressure differential across the aperture for a specific time or use of a manometer of a known volume displacement to draw the volume through the measuring aperture. Such methods, as those using the Coulter Counter aperture are considered non-focussed flow methods.

Alternatively, so called focussed flow systems for flow cytometry increasingly adopted for clinical laboratory use, provide data producing ratios and percentages, not absolute particle counts per microliter type counts. The sample stream is supported and surrounded by a particle free sheath liquid flow which steers the sample along a constant path in the flow chamber (flow cell). This applies to all flow cells whether optical, electrical or both. Once a steady state flow condition is established, data acquisition is started and occurs until something or someone stops such acquisition. The pressure which pushes the sample and the pressure which pushes the sheath liquid must remain constant throughout inorder to maintain the necessary stable flow. If the difference in the sheath to sample pressure is changed, the sample flow path may move or change in cross-section.

Conventionally, the normal mode of operating flow cytometers is to place a tube of sample before a pick-up probe, pressurize the sample and collect data until sufficient "events" are accumulated to provide acceptable statistics enabling the generate percent positive, percent negative, etc. Any incorporation of means to provide absolute counts using the flow cytometer technique must allow the normal mode of flow cytometric operation to be unimpeded.

SUMMARY OF THE INVENTION:

The herein invention provides a metering and transfer valve assembly particularly for use with a focussed flow cytometer, whereby to enable obtaining an absolute count of a liquid sample comprising particles dispersed in a suspension fluid medium in addition to the normal flow cytometry data acquisition, and, in addition, permitting switching the input to the flow chamber of the cytometer for all modes of operation between the normal manual sample aspiration station and the multiple carousel loader sources easily and without dead volume.

According to the invention, the liquid metering and transfer valve assembly comprising a pair of outer valve elements and an inner valve element arranged sandwiched between said outer valve elements, said outer valve elements being arranged in face to face frictional sealable engagement with the respective opposite faces of said inner valve element, at least a pair of said valve elements being translatable relative to said other one of said valve elements, said inner valve element having a pair of spaced parallel through passageways, one of said through passageways having a precise interior volume defining a metering chamber, the other of said through passageways defining a flow through passage, one of said outer valve elements having at least one through first entry passageway and a parallel through second entry passageway spaced from said first entry passageway, the other of said outer valve elements having at least first and second spaced parallel outlet passageways, at least one source of liquid sample, said valve elements being relatively translatable to place said metering chamber in communication with one of said entry passageways and one of said outlet passsageways to define a continuous flow path through said valve assembly, means to introduce a liquid sample to said one entry passageway, means to introduce a sample-inert fluid to the other entry passageway, said valve elements being selectively translatable to define a second flow path through said valve assembly including said other entry passageway, said metering chamber and one of said outlet passageways, means to lead said one of said outlet passageways to a testing location exterior of said valve assembly and means to lead the other one of said outlet passageways to a second location exterior of said valve assembly, said sample-inert fluid capable of driving the content of said metering chamber to the exterior testing location along said second flow path subsequent to definition of said second flow path.

BRIEF DESCRIPTION OF THE DRAWINGS

FIG. 4A is a plan view of the other, outer valve element (the front valve element) of the valve assembly of FIG. 2 illustrating the outer face thereof;

FIG. 4B is a plan view of the valve element of FIG. 4A illustrating the inner face thereof.

FIG. 4C is an elevational view of the valve element of FIGS. 4A and 4B, portions being shown in sectional representation;

FIG. 6 is an exploded, diagrammatic, isometric representation of the liquid metering and transfer valve assembly constructed in accordance with the invention and illustrated in the fill condition assumed by the valve assembly when the sample is obtained utilizing the conventional aspiration probe immersed in a sample container or the like;

DESCRIPTION OF PREFERRED EMBODIMENTS

Figure 1:
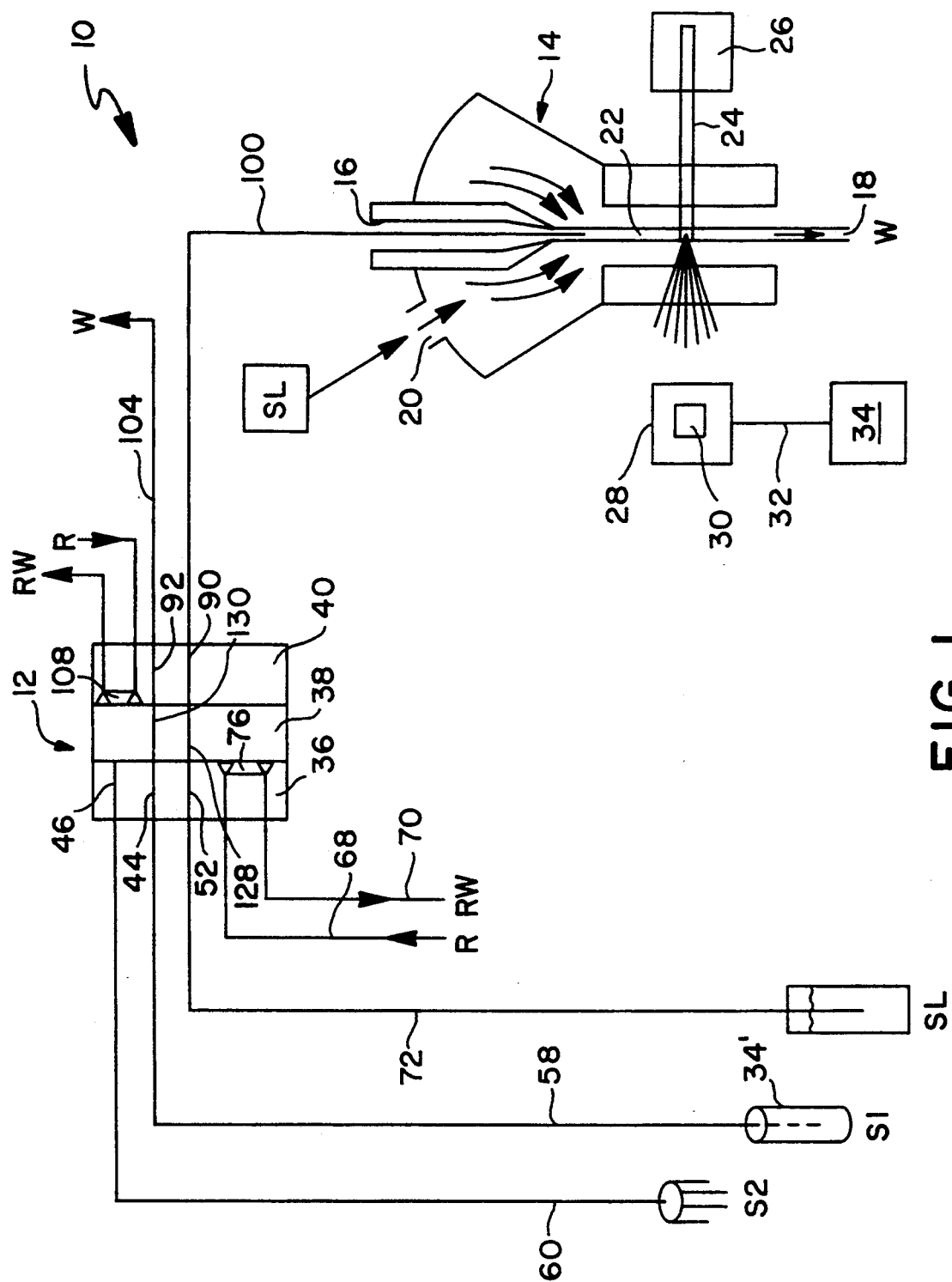
FIG. 1 is a diagrammatic representation of a focussed flow type of flow cytometer employing the liquid metering and transfer valve assembly constructed in accordance with the herein invention, said valve assembly being shown in the condition assumed during the Absolute Count stage of the treatment of sample manually obtained via an aspiration probe from a sample source.

This invention provides a liquid metering and transfer valve assembly particularly for use with a flow cytometer which enables the obtaining of conventional flow cytometric data for cell analysis, and, in addition, the obtaining of absolute count information, the first data being in the form of percentages and the second, uniquely provided data being in the form of an absolute count expressed as the quantity of particles per unit volume, from the same fluid sample from which the first mentioned data is taken. The second data factor is described as an Absolute Count and comprises a critical factor in monitoring patient clinical progress.

The metering and transfer valve assembly of the invention provides election for analysis of blood samples obtained from a so-called manual aspiration probe or a blood sample obtained from a carousel type automatic sampling unit which carries plural containers each holding pre-prepared blood samples, hereinafter referred to as a multi-carousel loader.

Particulate suspensions other than blood sample suspensions such as many cellular suspensions may be evaluated using the invention herein to obtain the Absolute Count thereof and the evaluation of the characteristics of such particulates can be effected. The use of calibrator compositions of known concentration can be utilized with the benefit of the Absolute Count obtained and applied to calibrate the cytometer type instruments.

The said valve assembly permits use as a passive flow through means for directing a blood sample, for example, from one or the other of said sources, in a continuous stream, to the focussed flow sensing means of the flow cytometer, and, as well, functions as a segmenting valve for metering and directing a precise volume aliquot of the same sample to the flow sensing means of said flow cytometer to provide an absolute count, i.e. number of cells per unit volume, of the cell bodies contained in the aliquot.

The said valve assembly enables a portion of the blood sample from the same source (probe or multicarousel loader) to be first directed to the flow cell of the flow cytometer for normal flow cytometric analysis, and then, segmented to define a precise volume thereof as an aliquot thereof, said aliquot then being transported to a path through which sheath fluid is flowed, driving said aliquot to the flow cell for obtaining an absolute count of all cells in said aliquot.

As will be observed, a continuous sample flow path is defined through the valve assembly, said sample flow path including a precise volume segmenting passage. The said sample flow path leads from the valve assembly to the sample intake of the flow chamber of a focussed flow cytometer, the sample, in a stream surrounded by a sheath liquid, is passed through the sensing portion of a focussed flow cytometer. A laser beam is passed at right angle through said flowing stream of liquid; detector means being provided to measure the fluorescence and/or light scattering originating by contact of the particles with the laser beam. When the aliquot of said sample is segmented from the flow path, the valve assembly operates to place said aliquot in the path of a sheath fluid introduced thereto and same is directed to said flow chamber and passed through said laser beam. Data representing the actual number of particles is acquired. Data is collected until the data rate approaches zero. Thus data representing the actual number of particles in the sample aliquot is acquired. Hence an absolute count is acquired, the volume being precise, known and actual reflective of all the particles within said aliquot.

Referring first to FIG. 1 wherein is illustrated, in generally flow diagrammatic representation, a flow cytometer system 10 in which the liquid metering and transfer valve assembly 12 constructed in accordance with the herein invention is incorporated as a part of the liquid handling system thereof. The flow cytometer system conventionally includes a flow chamber 14 (which may be referred to synonymously as a flow cell), the flow chamber 14 having a sample inlet 16 for receiving a sample containing particles such as stained blood cells to be monitored from a source S1, a waste outlet 18 and a sheath fluid inlet 20 for receiving a sheath fluid, such as isotonic saline, from a source SL thereof. The flow chamber 14 includes a detection station or area represented by 20' in FIG. 2 as the area crossed by the laser beam 24 through which the blood cells to be identified are passed while contained in a narrow stream or column 22 of sample liquid surrounded by particle free sheath fluid. A laser beam 24 from a laser mechanism 26 is directed through the column 22 toward detection device 28 which includes a photodetector 30. The laser beam 24 may consist of a single laser beam or plural laser beams which conventionally passes through the column 22 at right angle relative to the direction of flow of the stream.

Various types of cells can be detected by measuring the light scattered from the cell, as well as the fluorescent energy generated by the energized dye contained in the stained cells. The light scatter detected by the photodetector 30 provides data signals represented by line 32 directed to the analyzer 34 which collects and analyzes information from said data signals, such information generally regarding-number, size, optical density, granularity and other factors aiding in identifying the particular type of cell. The information, particularly the count information obtained via the conventional flow cytometer systems provide ratios and percentages rather than an Absolute Count (count per unit volume) and maintains a steady state flow condition flow condition. Conventionally, the liquid sample stream is supported and surrounded by a particle free sheath flow which may be an inert liquid steers the sample along a constant path within the flow chamber 14. This applies to all flow chambers whether optical, electrical or both. Once the steady state flow condition is established, the data aquisition is started and occurs until something or someone stops it. The pressure which pushes the sample and the pressure which pushes the sheath fluid must remain constant inorder to maintain the flow stable. If the difference in the sheath to sample pressure is changed, the sample flow path may move or change in cross-section. The sheath fluid remains in a reservoir SL where it is pressurized for the purpose of driving the sample to the flow chamber 14. Pressure is not the only force that can be utilized to direct the sample to the flow chamber, as vacuum or differential pressure are analogous. There is no mixing of the sheath fluid and sample within the flow chamber due to the laminar flow conditions present.

In conventional flow cytometers, the ratio between the sheath fluid volume flow rate and the sample bearing fluid flow volume rate may not be constant or predictable. Changes in conduit lengths and diameters, viscosities, temperature as well as pressure cause significant variations in the sheath to sample flow rate ratio. Commonly, the nature of the cytometer systems is such that the difference in sheath to sample pressure is very low, on the order of $\pm 0.2$ p.s.i. Even this small difference in pressure may cause significant changes in volume flow rate. Other flow introduction means, such as syringes or positive displacement pumps, have been employed to deliver the sample to the flow chamber but these have been difficult to maintain and implement.

In the system 10 diagrammatically illustrated in FIG. 1, the metering and transfer valve assembly constructed in accordance with the invention and designated by reference character 12 is disposed between the sample source S1 and the flow chamber 14 and has the capability of functioning to direct a volume of liquid sample directly to the flow chamber 14 of the flow cytometer system 10 and to meter, isolate and direct a precise volume portion or aliquot of the Same liquid sample to said flow chamber so as to enable an absolute count of the particles in that precise volume of liquid sample—i.e. number per precise volume unit. Depending upon the character and identity of the particle whose identity is to be monitored, where same is present along with many other type particles, precise absolute counts of specific cell types can be provided, the specific particles being distinguished from the other particles. In addition, many successive absolute counts can be made from that same liquid sample by repeatedly metering and isolating the aliquots one after another, the aliquot being isolated in a metering chamber and brought, for example, into a pressurized sheath fluid flow path, to be driven (or pushed) in a stream to the flow chamber surrounded by said sheath fluid.

The valve assembly 12 is similar in some respects to the conventional metering and transfer valve assemblies which have been employed in particle study systems operating in accordance with the Coulter principle, such as described in U.S. Pat. Nos. 2,656,508, 3,549,994 and others. Such valve assemblies have been described in U.S. Pat. Nos. 3,567,390, 4,152,391, 4,445,391, 4,507,977, 4,896,456 and 4,957,008 and others. The key, common to these prior patents, is the definition of a continuous flow path through the valve assembly, including a metering chamber defined by a passageway of precise interior volume called a segmenting passageway, and manipulating the valve assembly to segment from said flow path, the precise volume of sample within the segmenting passgeway and drive that sample volume from the valve assembly by introduction of a predetermined volume of diluent thereto, directing that sample and diluent to an exterior testing location. At that testing station, the resulting dilution is passed through a restricted aperture across which an electrical impedance is provided, each particle causing a change in the impedance within the aperture, said change being detected and analyzed.

The volume passed through the aperture is controlled by a providing a known differential pressure or use of a manometer for measuring the flow of the dilution constituting particles in fluid suspension or precisely timing the duration of flow through the measuring aperture. These instruments have been used to provide a count per unit volume and the results obtained were used with the conventional flow cytometer generated percentages to calculate a count per unit volume. This required that a cytometry laboratory have access to the relatively expensive electronic blood cell counter instrument or that the results obtained from such blood cell counter be supplied from each given patient. The potential for error is boundless. Mixing results from patient to patient, errors in recording and transfer and identification coordination of results from patient to patient, erronious identications of source and results, and the like. The need for multiplicity of blood samples required from each donor, reduction of accuracy and reproducibility of results, increased exposure to the biohazards of handling multiple blood samples and other problems are manifest. The best solution would be afforded to perform the absolute count, i.e. directly using the flow cytometer to actually count the population in question with known fresh blood—i.e. on the same blood from the same source as introduced normally into the flow chamber of the cytometer. The valve assembly according to the invention provides such solution, long sought but not previously obtainable.

Figure 2:
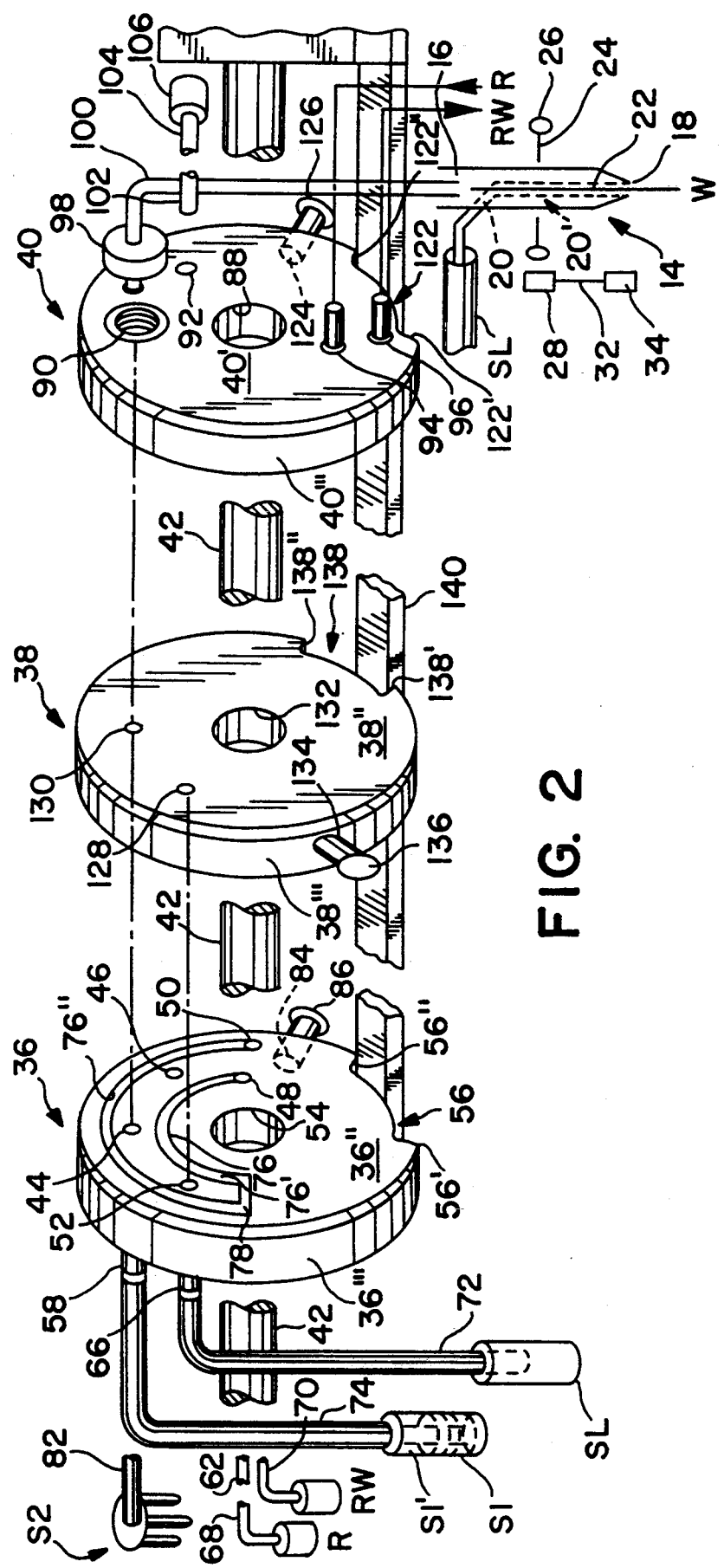
FIG. 2 is an exploded, diagrammatic, isometric representation of the liquid metering and transfer valve assembly constructed in accordance with the invention herein and illustrated in the normal condition, as distinguished from the condition of the valve assembly assumed during the obtaining of the Absolute Count of sample obtained via the aspiration probe such as illustrated in FIG. 1.
Figure 8:
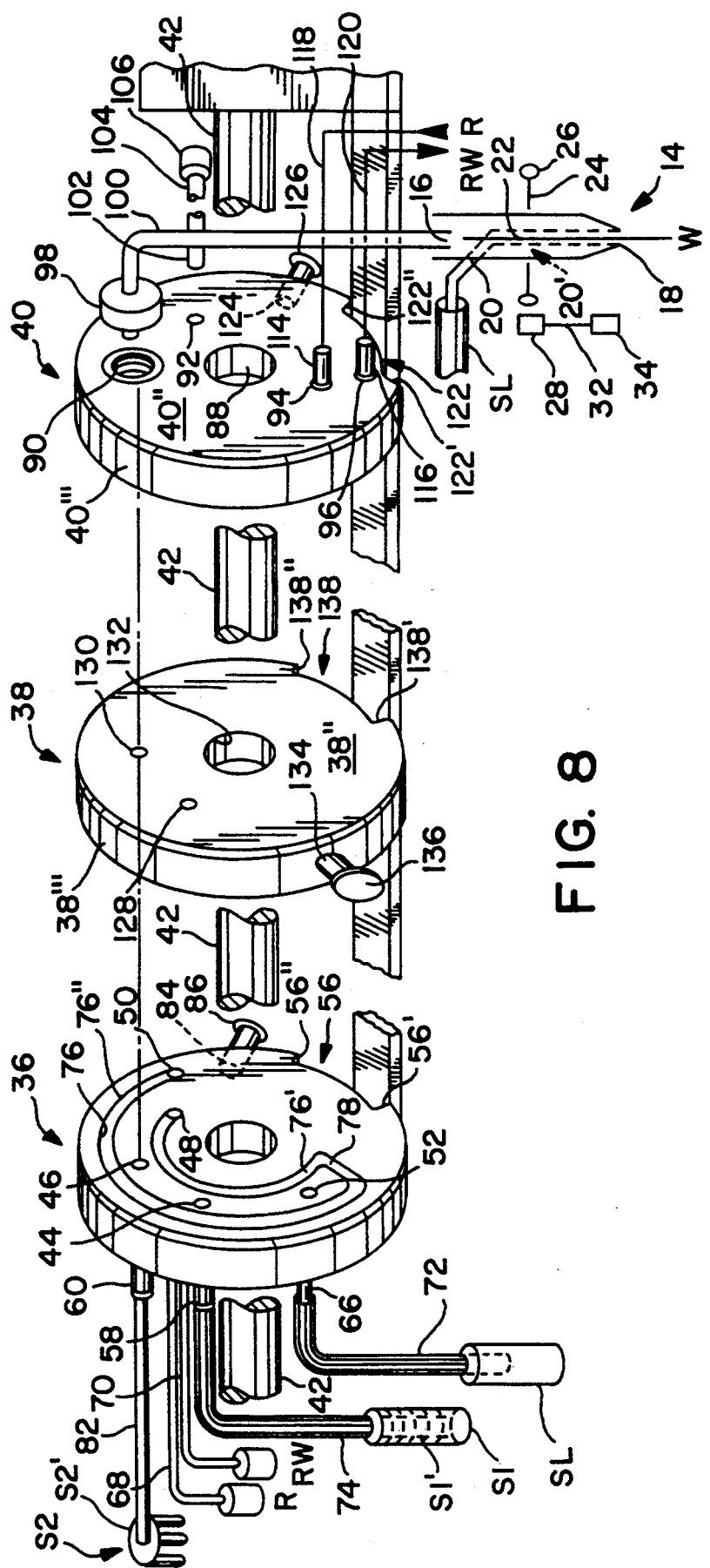
FIG. 8 is an exploded, diagrammatic, isometric representation of the liquid metering and transfer valve assembly constructed in accordance with the invention and illustrated in the normal condition, but where an alternative source of sample is utilized, such as a multiple sample carousel apparatus, in lieu of the source selected in the operations illustrated in FIGS. 2, 6 and 7.

It should be noted that the "normal" condition as illustrated in FIGS. 2 and 8 illustrate the a condition during the conventional cytometric analysis operation, i.e. normal cytometer operation. The transfer valve assembly 12 according to the invention comprises three like-dimensioned valve disc elements 36, 38 and 40 arranged coaxially aligned with the faces of the center element 38 frictionally sealably engaged with the adjacent faces of the outer valve disc elements 36 and 40. The elements 36, 38 and 40 are mounted on shaft 42, each for limited rotation one relative to the others. Conventionally, one of the prior valve disc elements was required to remain stationary to provide a stationary point of reference. Each of the valve disc elements is provided with through passageways, the center valve element being provided with at least one precise volume through passageway described as the segmenting passageway. The passageways carried by the other valve disc elements can be described generally as flow conducting passageways as they were used to define at least one continuous flow path through the valve assembly and to provide flow paths employed to introduce diluent to the segmenting passageway for enabling direction of the sample carried by the segmenting passageway to a location exterior of the valve assembly per normal usage thereof. Segmenting passageways could be provided in the other valve disc elements, say by accommodating the ends of loops which contain precise volumes of liquid therein and which are included in the continuous flow path for sample. Heretofore, all these prior valve assemblies were utilized to provide dilutions of the sample aliquots isolated in the segmenting passageways defined therein. None of the valve assemblies were employed merely to isolate a precise volume of sample as an aliquot and transfer (and deliver) that specific volume of sample intact to an exterior location, or to function to define a direct flow path for undiluted liquid sample likewise to an exterior location—i.e. as passive flow for examination.

As will be described, only one segmenting passageway is provided in the valve assembly 12 described as the preferred embodiment of the invention. For the purpose of this description, the valve disc element 36 shall be described as the rear element of the valve assembly 12 and the valve disc element 40 shall be described as the front element of valve assembly 12. The valve disc element 38 shall be described as the center element of the valve assembly 12 and carries the segmenting passageway.

Valve assembly 12 is capable of receiving liquid sample from one of two sources per operation, the first source S1 being obtained manually from reservoir S1' (FIGS. 2,6,7,8,9) or, as more commonly, from a single sample tube 34' (FIG. 1). The second source S2 from which valve assembly 12 can receive liquid sample can be described as an automatic sampler S2' where a plurality of sample tubes (not shown) are placed in individual sockets (not shown) carried by a turntable device (also not shown) automatically sequentially stepped to provide a continuous sequence of drawn liquid samples. This shall be described as an automatic sampler or a multiple carousel loader.

Figure 3C:
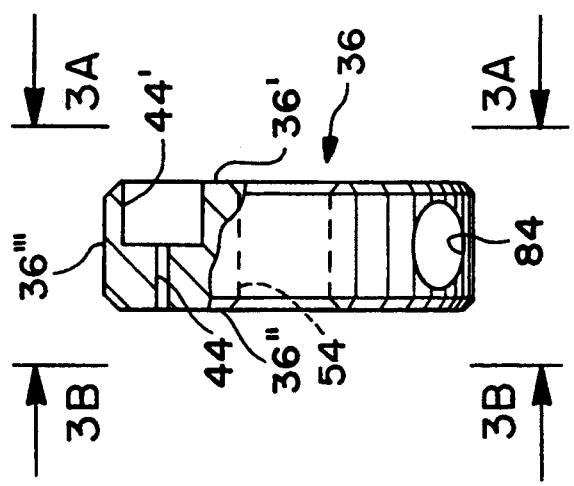
FIG. 3C is an elevational view of the valve element of FIGS. 3A and 3B, portions being shown in sectional representation.
Figure 3B:
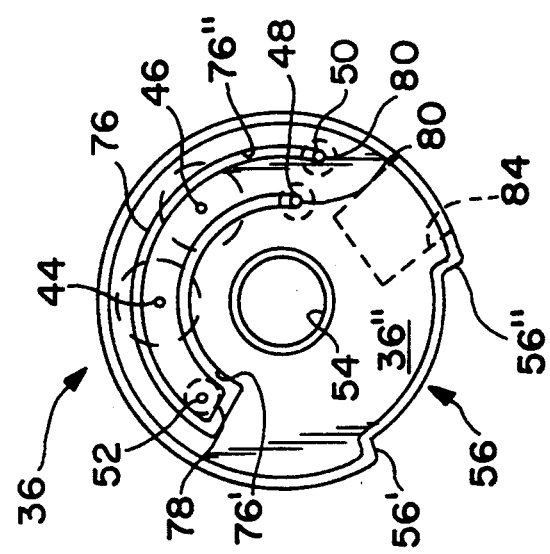
FIG. 3B is a plan view of the valve element of FIG. 3A illustrating the outer face thereof.
Figure 3A:
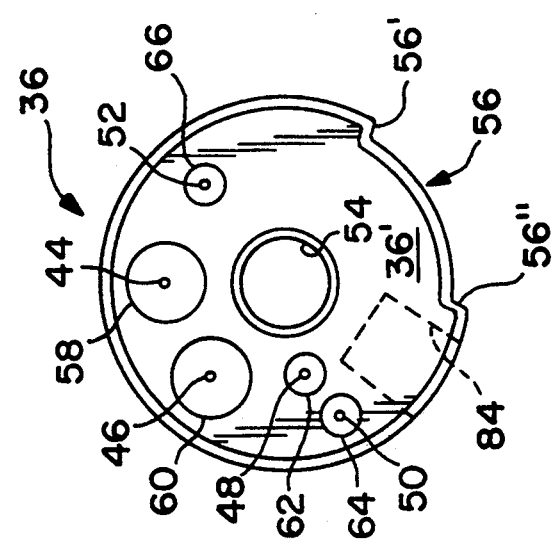
FIG. 3A is a plan view of one of the valve elements (the rear valve element) of the valve assembly of FIG. 2.
Figure 5C:
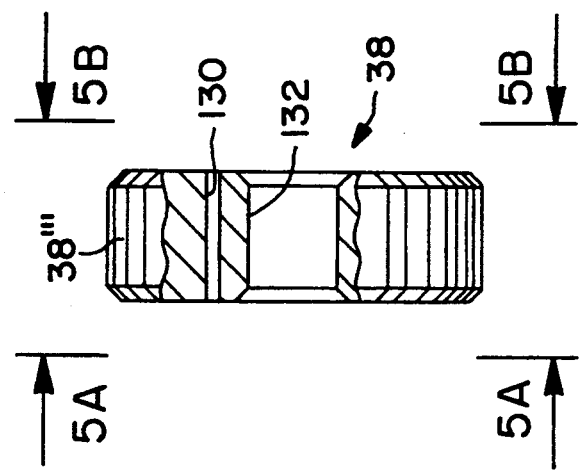
FIG. 5C is an elevational view of the center valve element of FIGS. 5A and 5B, portions being shown in sectional representation.
Figure 5B:
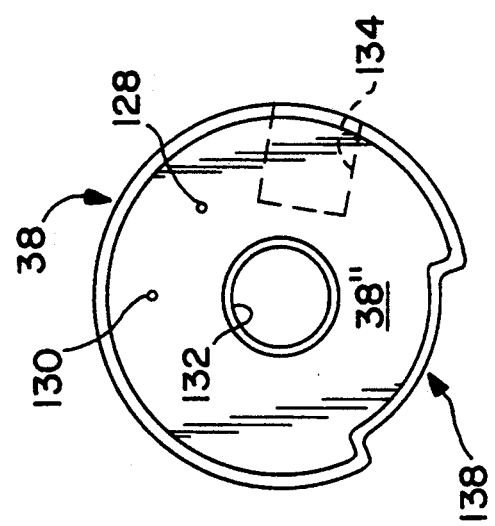
FIG. 5B is a plan view of the center valve element illustrated in FIG. 5A but showing the opposite face thereof.
Figure 5A:
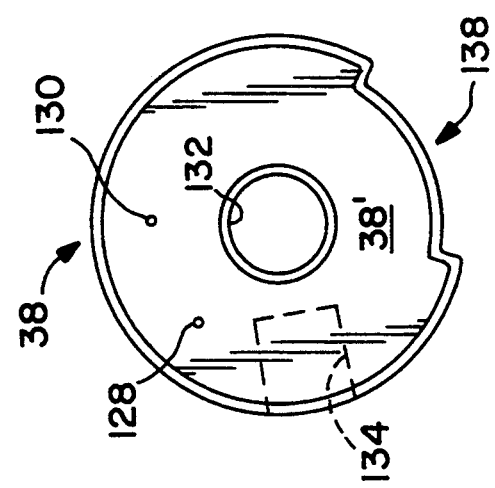
FIG. 5A is a plan view of the center valve element of the valve assembly of FIG. 2.
Figure 6:
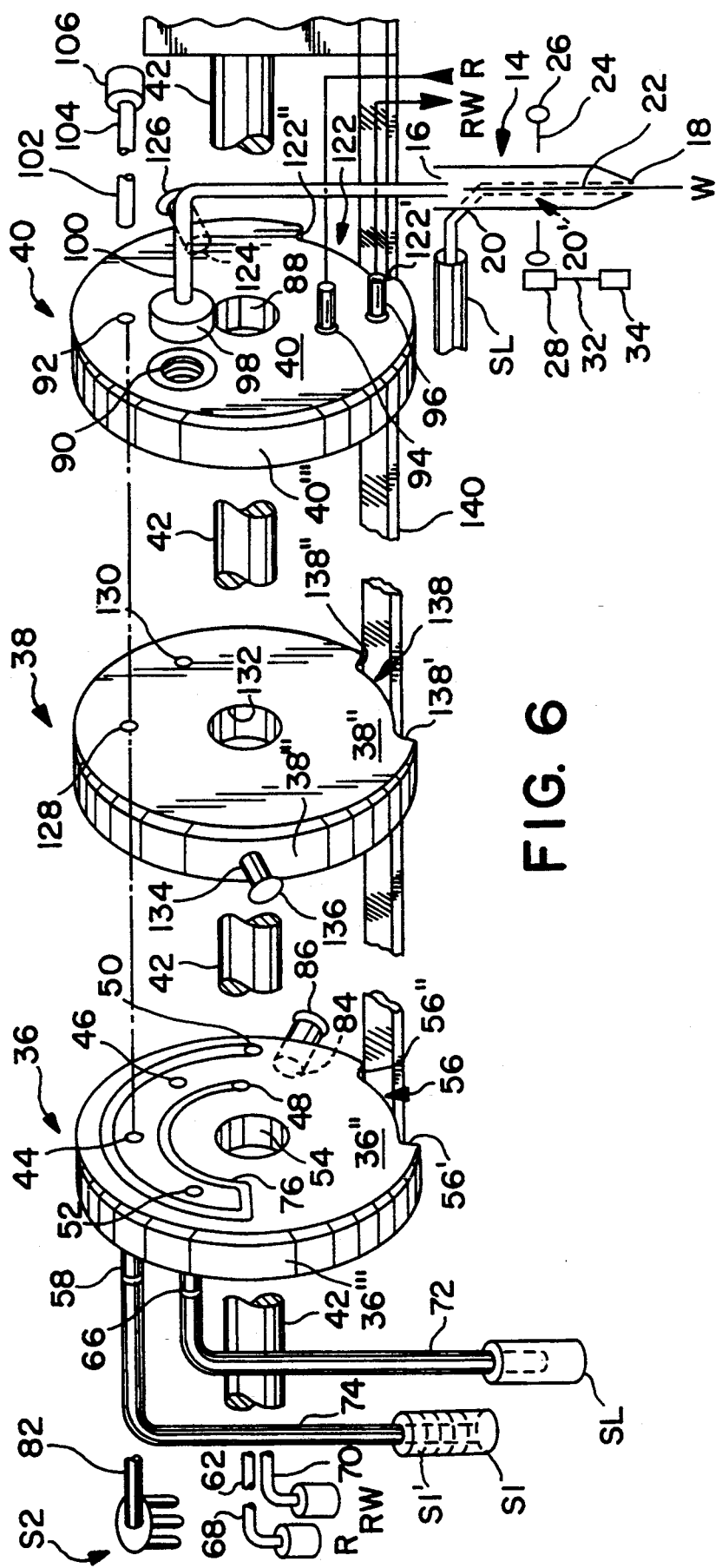
Figure 7:
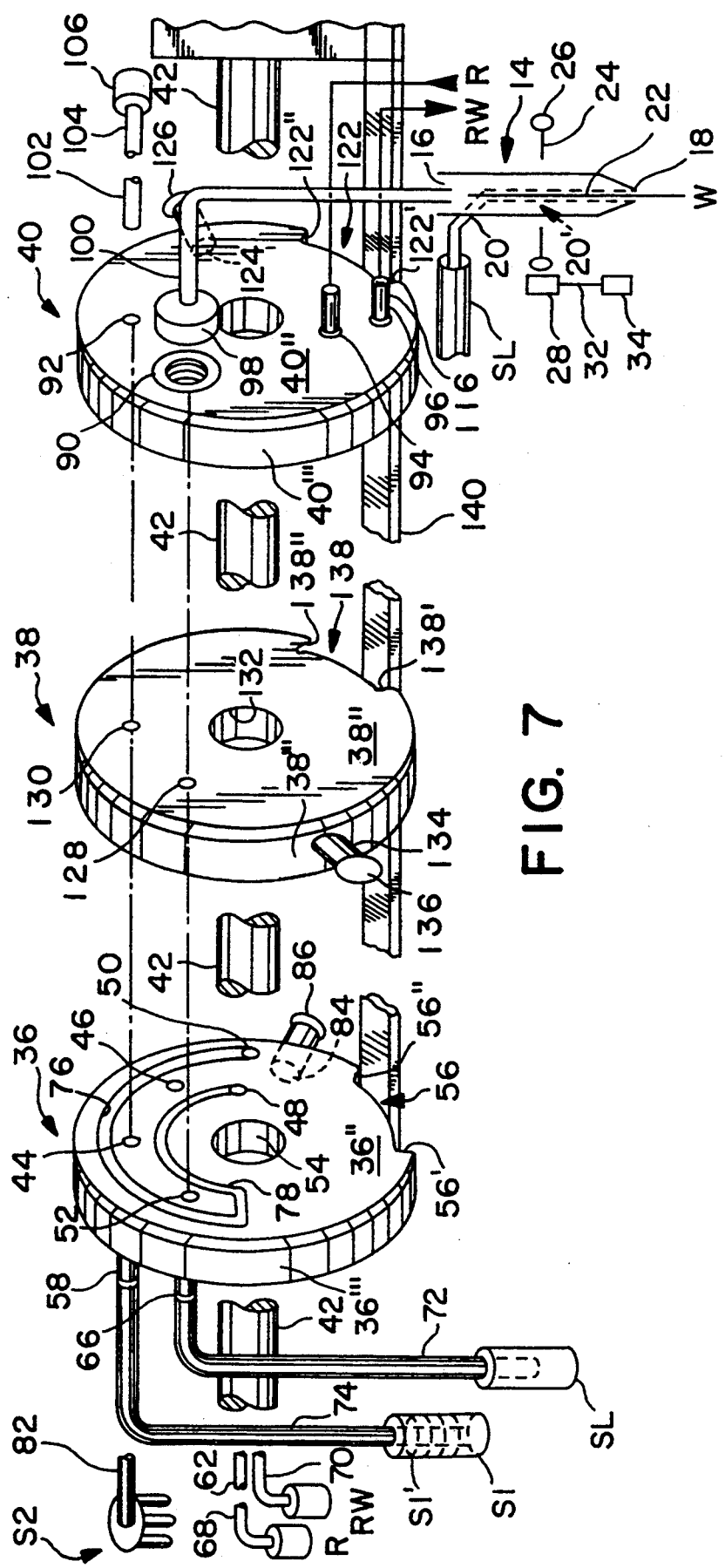
FIG. 7 is an exploded, diagrammatic, isometric representation of the liquid metering and transfer valve assembly constructed in accordance with the invention and illustrated in the condition assumed thereby for the purpose of obtaining the Absolute Count in respect of a sample obtained employing the aspiration probe, i.e. the sample treated in FIGS. 2 and 6.

The rear valve disc element 36 is illustrated in FIGS. 3A, 3B and 3C; the front valve disc element 40 is illustrated in FIGS. 4A, 4B and 4C; and the center valve disc element 38 is illustrated in FIGS. 5A, 5B and 5C. The normal condition or stage of operation of the valve assembly 12 is illustrated in FIG. 2; the fill condition assumed by the valve assembly 12 is illustrated in FIGURE 6; and the count condition assumed by the valve assembly 12 is illustrated in FIG. 7. The FIGS. 2, 6 and 7 related to the treatment of a sample obtained via the aspiration probe, i.e. represent the conditions of the valve assembly assumed when the source of sample is S1 while the conditions represented in FIGS. 8 and 9 occur when the source of sample is S2. The count condition represented in FIG. 7 occurs when the source of sample is S1.

FIG. 3A illustrates the outer face 36' of rear valve disc element 36. Through passageways 44 and 46 are formed in valve disc element 36 as are through passageways 48, 50 and 52. Rear valve disc element 36 carries axial central passage 54 to enable mounting thereof on shaft 42. Passageways 44, 46, 48, 50 and 52 are axially parallel to the axial central passage 54. The rear valve disc element 36 is provided with circumferential arcuate notch 56 opening to the outer circumference 36''' of valve disc element 36 to define the limits for rotating said valve disc element 36. Passageways 44 and 46 open into large diameter internally threaded recesses 44' and 46' for receiving externally threaded nipples 58 and 60 to provide coupling to the respective sample sources S1 and S2 respectively. Nipples 62, 64 and 66 are seated in passageways 48, 50 and 52 respectively, to enabling coupling of conduits 68, 70 and 72 thereto. Conduits 68 and 70 lead respectively to a rinse liquid source R and a rinse liquid waste receptacle RW. Conduit 72 is adapted to be coupled to nipple 72 for feeding sheath liquid to passageway 52 from the source of sheath liquid SL. The respective passageways carried by the rear valve disc element 36 open to the inner surface 36'' of the valve disc element 36 as represented in FIGS. 3B and 3C.

The inner face 36'' of valve disc element 36 is provided with semi-arcuate catch channel 76 consisting of a pair of semi-arcuate inner and outer grooves 76' and 76'' joined by radial groove 78 and arranged spaced from the openings of passageways 44, 46 and 52, said grooves 76' and 76'' lying along concentric radially spaced arcs. Each groove 76' and 76'' have ends 80, with passageways 48 and 50 opening thereinto. Radial groove 78 completes the catch channel 76 which serves to prevent any material, liquid or otherwise, from traveling from the junctions of the respective through passageways to the inner or the outer circumferential portions of the rear valve disc element 36. Rear valve disc element 36 is provided with threaded recess 84 to accommodate threaded radially outwardly extending threaded pin 86 insertable thereinto enable the rear valve disc element 36 to be rotated within the limits defined by the opposite ends 56' and 56'' of cicumferential notch 56 whereby selectively to position the rear valve disc element during the operational cycle of the valve assembly 12.

Reference now is made to FIGS. 4A and 4B wherein the outer face 40' and the inner face 40'' of front valve disc element 40 respectively are illustrated. The front valve disc element 40 carries a central axial through passage 88 for mounting said element 40 on shaft 42. Front valve disc element 40 carries through flow conducting parallel through passageways 90 and 92. Element 40 also carries an additional pair of through passageways 94 and 96. Passageways 90 and 92 open to the opposite faces 40' and 40'' of valve disc element 40 while passageways 94 and 96 also open to the opposite faces 40' and 40'' of valve disc element 40. The outer face of front valve disc element 40 is provided with threaded recess 90' concentric with passageway 90. Threaded tubular nipple 98 is engaged within threaded recess 90' for coupling passageway 90 to the flow chamber sample feed line 100 leading to the sample inlet 16 of the flow chamber 14. Liquid passive flow conducting passageway 92 of front valve disc 40 opens to the inner surfaces 40' and 40'' of front valve disc element 40. Nipple 102 is received within the passageway 92 at its opening to the outer surface 40' of front valve disc element 40 for coupling to conduit 104 leading to a waste reservoir 106. Passageways 94 and 96 also open to the opposite surfaces 40' and 40'' of valve disc element 40. The inner surface 40' of front valve disc element 40 carries catch channel 108 angularly displaced relative to the disposition of catch channel 76 formed in the inner surface 36'' of rear valve disc element 36. Catch channel 108 comprises a pair of arcuate groove lengths 108' and 108'' of generally uniform cross section respectively formed along concentric arcs respectively along the inner and outer circumferential surfaces of the said inner surface 40''. Grooves 108' and 108'' have a pair of ends 110. A radial groove 112 connects said grooves 108' and 108'' to complete the catch channel 108. Passageways 94 and 96 open to said ends 110. Nipples 114 and 116 are introduced into the outer surface openings of passageways 94 and 96, said nipples enabling coupling of conduits 118 and 120 leading respectively to the source of rinse liquid for flushing the catch channel 108 and to the waste reservoir RW for rinse liquid.

Circumferential notch 122 is formed in the outer circumferential surface 40''' of front valve disc element 40 opening to the outer circumferential surface 40''''. The walls 122' and 122'' define the limits of rotation of said front valve disc element 40. Threaded recess 124 is formed in the outer circumferential surface 40'''. Threaded pin 126 is seated within recess 124 and extends radially outward therefrom so as to enable rotation of said front valve disc element 40 between the limits represented by the walls 122' and 122'' of notch 122.

Reference is made to FIGS. 5A, 5B and 5C wherein the center valve disc element 38 of the valve assembly 12 is illustrated, FIGS. 5A and 5B showing the opposite faces 38' and 38'' of said center valve disc element 38. Center valve disc element 38 carries a precise volume through passageway 128 which is defined as a segmenting passageway and functions as a measuring chamber. Center valve disc element 38 also carries a flow conducting (passive) passageway 130 angularly spaced from passageway 128 and which is axially parallel thereto, both passageways 128 and 130 opening to the opposite surfaces 38' and 38'' of said central valve disc element 38. Center valve disc element 38 also is provided with central axial passageway 132 for mounting said element 38 on shaft 42. Threaded recess 134 is formed in the outer circumferential surface 38''' of element 38 opening to said outer circumferential surface 38''' thereof. Threaded pin 136 is seated therein to enable rotation of said element 38 through the limits defined by the walls 138' and 138'' of circumferential notch 138 also provided in the outer circumferential surface 38''' of said center valve disc element 38. In the illustrated embodiment, the passive flow conducting passageway 130 is narrower in diameter than the segmenting passageway 128 because of the greater volume required for the aliquot.

Directing attention to FIG. 2, the valve assembly according to the invention is illustrated in its normal or rest condition when the source of liquid sample, blood, is S1 and to which the valve assembly 12 is returned when the Absolute Count condition is terminated. Rinsing or backwash of the valve assembly 12 takes place while the valve assembly is disposed in its normal condition. The conditions illustrated in FIGS. 6 and 7 also involve the source of the liquid sample being S1.

When the valve assembly is assembled on the shaft 42, a restraining bar 140 is seated fixedly within the circumferential notches 56, 122 and 138. The radially outwardly extending pins 86, 126 and 136 are coupled to respective pistons 142, 144 and 146 of fluid operated cylinders 148, 150 and 152 to enable rotation of the respective valve disc elements selectively so as to place said elements and their respective passageways as required for the operational stages in the cycle of operation of said valve assembly 12.

When the valve assembly 12 is in its normal condition illustrated in FIG. 2, the rear valve disc element and the front valve disc element are positioned so that the restraining bar 140 is engaged with limit 56" of circumferential notch 56 and with the limit 122" of circumferential notch 122, The center valve disc element 38 is positioned so that limit 138' of the circumferential notch 138 is engaged by the restraining bar 140. The sheath liquid entry passageway 52 and the segmenting passageway 128 are aligned. The inner surface 40' of front valve disc element 40 blocks the segmenting passageway 128. The S1 sample entry passageway 44 is aligned with the passive flow passageway 130 and the flow chamber directing passageway 90. The liquid sample is aspirated from the source S1 and directed to the S1 sample entry passageways 44, through the passive flow passageway 130 and the flow chamber directing passageway 90 to the flow chamber 14 to accomplish the normal cytometer analysis run. The flow conducting passageway 92, which can also be termed the waste outlet passageway and the S2 sample entry passageway 46 are blocked by the center valve disc element 38.

Referring to FIG. 6, the valve assembly 12 has been manipulated rotating the center valve disc element 38 clockwise and the front valve disc element 40 counter-clockwise from their position in FIG. 2 to place said valve assembly 12 in the fill condition. When the valve assembly 12 is disposed in the fill or load condition, the S1 sample entry passage 44, the segmenting passageway 128 and the passive flow conducting passageway 92 are aligned. Again the liquid sample S1 is introduced to the sample entry passageway 44 passing through the segmenting passageway 128 and the passive flow conducting passageway 92 and is directed to the waste reservoir while the segmenting passageway 128 is being filled.

The valve assembly 12 again is manipulated from the condition represented in FIG. 6 to assume the condition represented in FIG. 7, i.e. the Absolute Count condition. The center valve disc element 38 is rotated counter-clockwise from its fill position (FIG. 6) to place the segmenting passageway 128 in alignment with both the sheath fluid entry passageway 52 and the flow chamber directing passageway 90. Pressurized sheath liquid from source SL is introduced to the sheath liquid entry passageway 52 pushing the content of the segmenting passageway 128 to the flow chamber 14. The count is initiated and continues until the data flow picked up by the detector reaches a trailing number, i.e. little or no generated data pulses being picked up. The count then is considered complete and the Absolute Count is considered as having been obtained. The total number of particle (cell) bodies in the aliquot have been scanned and counted. Since the volume of the aliquot is known and all the particles (cells) therewithin are counted, the count is considered to be the Absolute Count. Note that the aliquot thus obtained is from the same sample that has been just cytometrically studied.

As discussed hereinbefore, the valve assembly 12 according to invention herein affords the opportunity to choose the source of sample between sample S1 and sample S2 (the sample originating via the multiple carousel loader). The valve assembly 12 is illustrated in FIG. 8 in the condition thereof where the sample source is S2 and the valve assembly 12 has assumed the "normal" condition for said sample S2.

In the normal condition for treating the S2 sample, the rear valve disc element 36 is NOT in the same orientation as assumed when the sample S1 is treated. The rear valve disc element 36 had been rotated counter-clockwise from its condition illustrated in FIG. 6 to the condition represented in FIG. 8. The center valve disc element 38 is positioned with the restraining bar 140 engaged with the wall 138' of notch 138. The front valve disc element 40 is oriented with the restraining bar 140 engaging wall 122" of notch 122. Now the S2 sample entry passageway 46 is aligned with the passive flow conducting passageway 130 and the flow chamber directing passageway 90. The S2 sample flow is initiated so that S2 liquid sample passes through S2 sample entry passageway, the passive flow conducting passageway 130 and the flow chamber directing passageway 90 and is introduced into the flow chamber 14 for cytometric examination.

Figure 9:
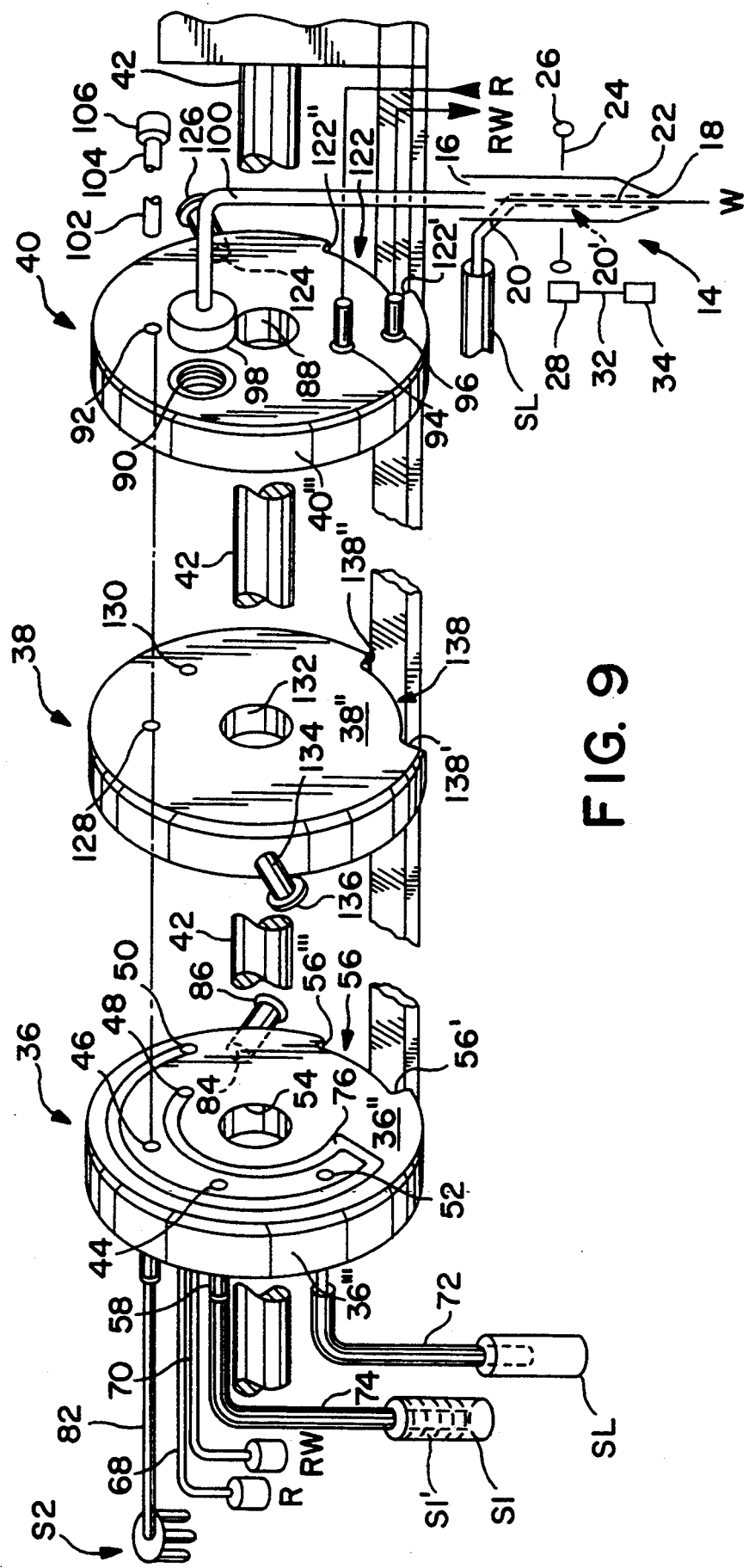
FIG. 9 is an exploded, diagrammatic, isometric representation of the liquid metering and transfer valve assembly represented in FIG. 8 using as a sample source, the alternative source, and shown in the fill condition; and, FIGS. 10A to 10E are diagrammatic representations respectively illustrating the system operations during the conditions represented by FIGS. 2, 6, 7, 8 and 9, respectively.
Figure 10A:
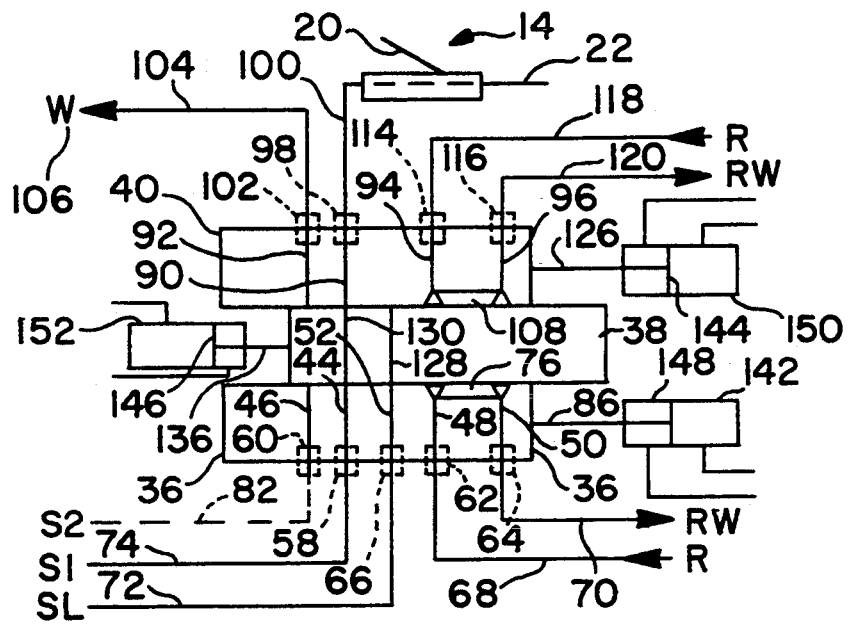
Figure 10B:
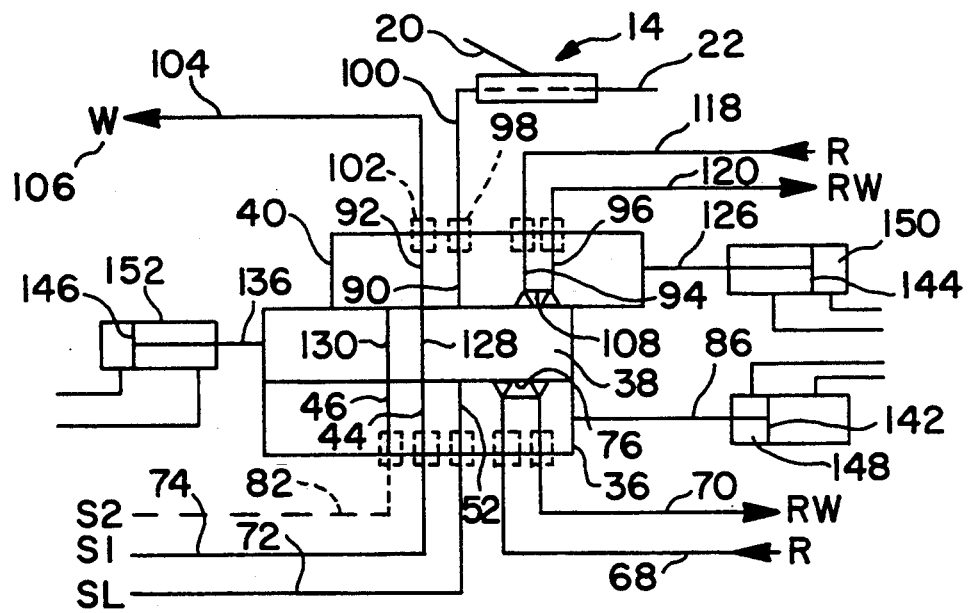
Figure 10C:
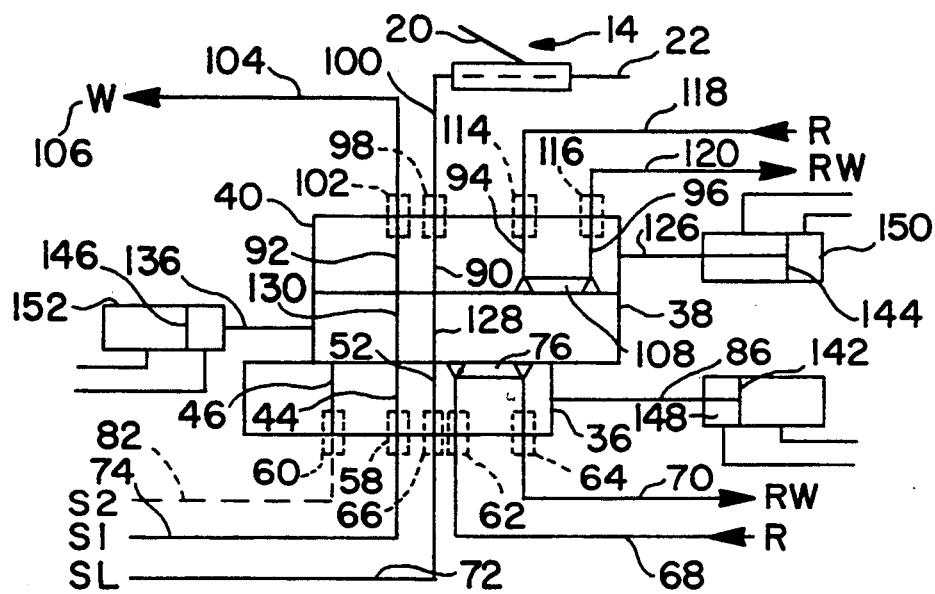
Figure 10D:
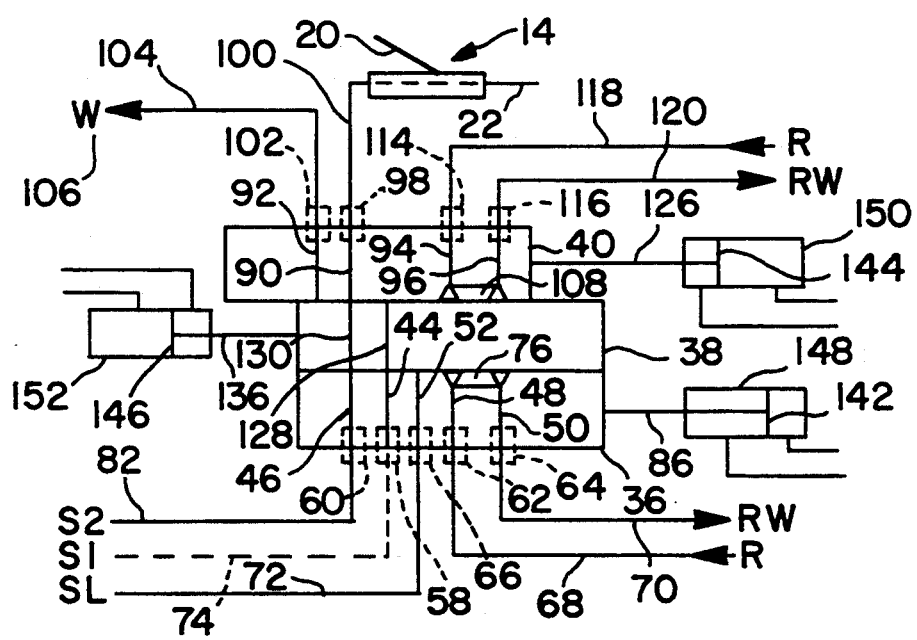
Figure 10E:
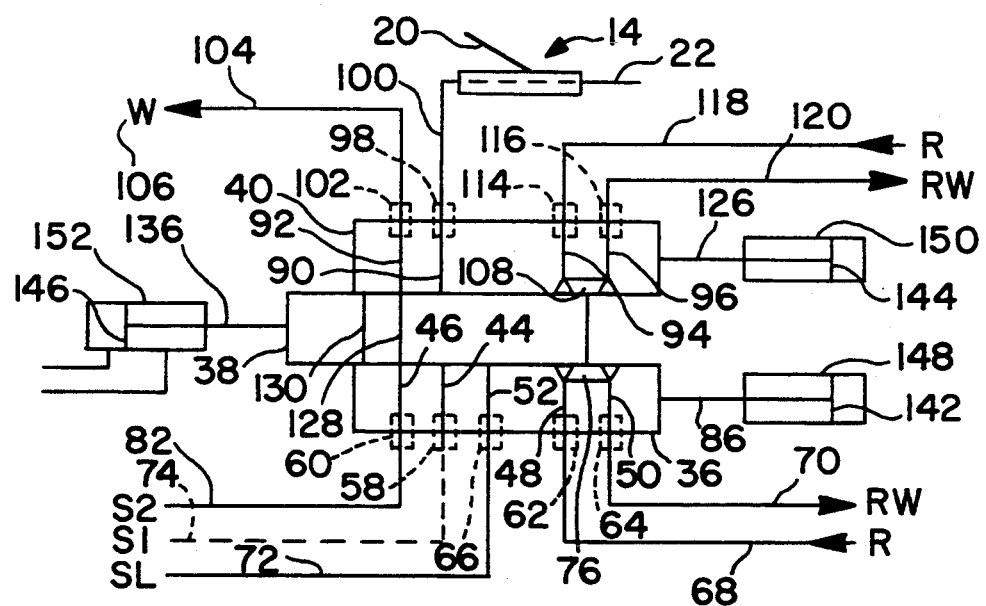

In FIG. 9, the valve assembly 12 has been manipulated from the normal condition of FIG. 8 to assume the fill condition there illustrated. The center valve disc element 38 is rotated clockwise from its normal condition to place the restraining bar 140 engaged with wall 138" of notch 138. The front valve disc element 40 has been rotated counter-clockwise from its normal position in FIG. 8 so that the restraining bar 140 engages wall 122' of notch 122. The rear valve element 36 is not manipulated from its position illustrated in FIG. 8, i.e. is in the same position to which it was translated to assume the position held in FIG. 8. The S2 liquid sample is introduced to the S2 sample entry passageway 46 and passes through segmenting passageway 128, continuing through the flow conducting passageway 92 and travelling to the waste reservoir W. Thus a continuous flow path including passageway 46, passageway 128 and passageway 92 is defined.

At this time, the valve assembly 12 is manipulated to assume the condition for obtaining the Absolute Count of the sample from source S2. Front valve disc element 40 remains unchanged. Now, the valve assembly 12 has reached the condition for obtaining the Absolute Count of the S2 sample. In order to reach the fill condition for sample S2, the rear valve disc element 36 is rotated clockwise and, simultaneously, the center valve disc element 38 is rotated counter-clockwise segmenting the now continuous body of sample to isolate the precise volume of aliquot within said segmenting passageway 128. The sheath liquid entry passageway 52 is aligned with segmenting passageway 128 and flow chamber directing passageway 90. The sheath liquid now is introduced into the sheath liquid entry passageway and drives the isolated S2 aliquot through the flow chamber directing passageway and thence to the flow chamber. The count is initiated and continues until stopped when the data flow reaches a trailing number, i.e. little or no data pulses being picked up by the detector so that one can safely assume that all the particles in said aliquot have been counted. The count condition of the valve assembly 12 has the respective valve disc elements thereof oriented the same regardless whether the sample source is S1 or S2.

In both the analysis of the S1 and S2 samples, when the valve assembly 12 is manipulated to return same to the particular normal condition, rinse liquid is introduced to both respective catch channels 76 and 108 to flush said channels.

It should be understood that while the preferred embodiment of the invention provides for alternation between S1 and S2 sample sources, merely one sample entry passageway may be provided so that both the cytometric scanning normally obtained and the Absolute Count measurement of an aliquot of the same so examined sample may be able to be obtained.

The operation of the valve assembly 12 also is represented diagrammatically in FIGS. 10A to 10E. The same reference characters used in FIGS. 2 through 9 are utilized to denote the same elements in FIGS. 10A to 10B and reference can be made to the earlier description in this specification. For convenience, the FIGS. 10A to 10E are located each on the same sheet of the drawings as carrying the respective FIGS. 2,6,7,8 and 9 with which they are coordinated. Note the full extension of the piston rods of the respective air cylinders as well as the fully retracted piston rods of certain of the air cylinders, all as represented in FIGS. 10A to 10E, to show the positioning of the respective valve disc members in reaching the respective operating conditions, as described in reference to FIGS. 2, 6, 7, 8 and 9 respectively.

Variations may occur to ones skilled in this art without departing from the spirit and scope of the invention as defined in the appended claims.

What is claimed is:

1. A method of cytometrically studying the characteristics of particles in liquid suspension comprising the steps of:
   a. providing a continuous first flow of liquid sample suspension for a predetermined duration from a source thereof;
   b. directing said flow to flow scanning means;
   c. isolating a precise aliquot volume of said liquid sample suspension from said continuous first flow thereof;
   d. directing said isolated aliquot volume to said flow scanning means; and,
   e. monitoring the passage of said isolated aliquot volume through said flow scanning means to establish an absolute count of the number of particles within said isolated aliquot volume independent of the total fluid flow through said flow scanning means.

2. The method according to claim 1 and the step of propelling said aliquot volume to said flow scanning means under the force of pressurized fluid applied thereto.

3. The method according to claim 1 and the steps of:
   providing at least two sources of liquid sample suspension;
   establishing alternate first flow paths for each of said sources of liquid sample leading to said flow scanning means;
   electing one or the other of said alternate first flow paths;
   establishing an additional dedicated flow path leading to said flow scanning means;
   introducing the liquid sample suspension from one of said sources to said elected alternate first flow paths;
   directing the liquid sample suspension from one of said sources along the elected alternate first flow path to the flow scanning means for a predetermined duration and scanning the passage thereof therethrough;
   isolating a precise aliquot volume of liquid sample suspension from said elected alternate first flow path;
   transferring said aliquot volume to said additional flow path and introducing pressurized inert fluid from a source thereof thereto, propelling said entire aliquot volume to said flow scanning means and scanning the passage thereof therethrough generating signals representative of said scanning;
   the scanning being continued until the signals representative of said scanning have materially diminished,
   whereby an absolute number of particles within said aliquot volume has been established.

4. The method according to claim 1 and the steps of;
   providing at least two sources of liquid sample suspension;
   establishing alternate first flow paths for each of said sources leading to flow scanning mean;
   electing one or the other of said alternate first flow paths;
   establishing an additional dedicated flow path leading to said flow scanning means;
   introducing the liquid sample suspension from one of said sources to said elected alternate first flow path;
   directing the liquid sample suspension from one of said sources along the elected alternate first flow path to the flow scanning means for a predetermined duration and scanning the passage thereof therethrough;
   isolating a precise aliquot volume of liquid sample suspension from said elected alternate first flow path;
   transferring said aliquot volume to said additional flow path and introducing pressurized inert fluid thereto, propelling said entire aliquot volume to said flow scanning means and scanning the passage thereof therethrough generating signals representative of said scanning;
   the scanning being continued until the signals representative of said scanning have materially diminished
   whereby an absolute number of particles within said aliquot volume has been established.

5. A cytometric method of determining the number and characteristics of particles in liquid sample suspension comprising the steps of:
   delivering a first flowing stream of liquid sample suspension continuously for a predetermined duration to a cytometer flow cell sheathed by an inert sheath fluid;
   establishing an energy beam in intercepting relation to said first flowing liquid sample stream;
   monitoring said energy beam as said first flowing sample stream passes through said cytometer flow cell;
   generating first signals representative of the effect upon said energy beam passing through the first flowing sample stream;

isolating an aliquot portion of said first flowing stream from said first flowing stream and driving the entire aliquot portion in a second flowing stream to and through said cytometer flow cell under the force of a pressurized inert fluid;

monitoring said second flowing stream as said second flowing stream passes through said cytometer flow cell and generating second signals representative of the effect upon said energy beam passing through said second flowing stream, said monitoring continuing until a materially diminished signal is observed;

whereby an absolute count can be established of the total number of particles within said aliquot portion of the same liquid sample stream as passed in said first flowing stream through said cytometer flow cell.

* * * * *